United States Patent
Rode et al.

(10) Patent No.: US 8,975,421 B2
(45) Date of Patent: Mar. 10, 2015

(54) PROCESS FOR PREPARATION OF γ-VALEROLACTONE VIA CATALYTIC HYDROGENATION OF LEVULINIC ACID

(71) Applicant: Council of Scientific and Industrial Research, New Delhi (IN)

(72) Inventors: Chandrashekhar Vasant Rode, Maharashtra (IN); Amol Mahalingappa Hengne, Maharashtra (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 13/774,048

(22) Filed: Feb. 22, 2013

(65) Prior Publication Data
US 2013/0296579 A1    Nov. 7, 2013

(30) Foreign Application Priority Data
Mar. 7, 2012    (IN) .......................... 0662/DEL/2012

(51) Int. Cl.
*C07D 307/00*    (2006.01)
*C07D 307/33*    (2006.01)

(52) U.S. Cl.
CPC .................................. *C07D 307/33* (2013.01)
USPC ....................................................... 549/326

(58) Field of Classification Search
CPC ..................................................... C07D 307/33
USPC ............................................................ 546/326
See application file for complete search history.

(56) References Cited

U.S. PATENT DOCUMENTS

2012/0197029 A1 *   8/2012   Hwang et al. ................. 549/266

OTHER PUBLICATIONS

Hengne et al. Green Chem., 2012, 14, 1064.*

* cited by examiner

*Primary Examiner* — Nizal Chandrakumar
(74) *Attorney, Agent, or Firm* — Ladas & Parry LLP

(57) ABSTRACT

An industrially viable process for selective preparation of γ-valerolactone using recyclable non noble metal catalyst is provided. This process provides 80-100% conversion to γ-valerolactone, with selectivity in the range of 80-100%.

13 Claims, 17 Drawing Sheets
(16 of 17 Drawing Sheet(s) Filed in Color)

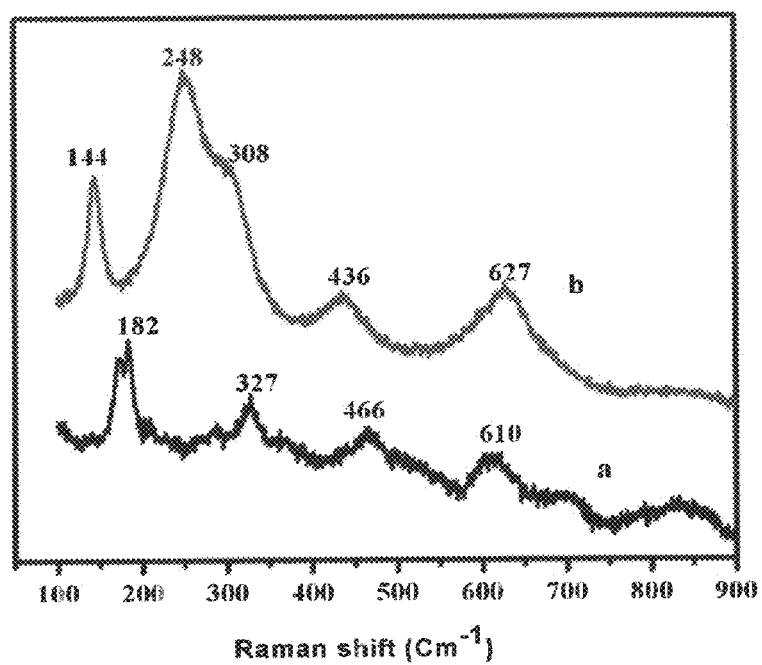
Fig: 2

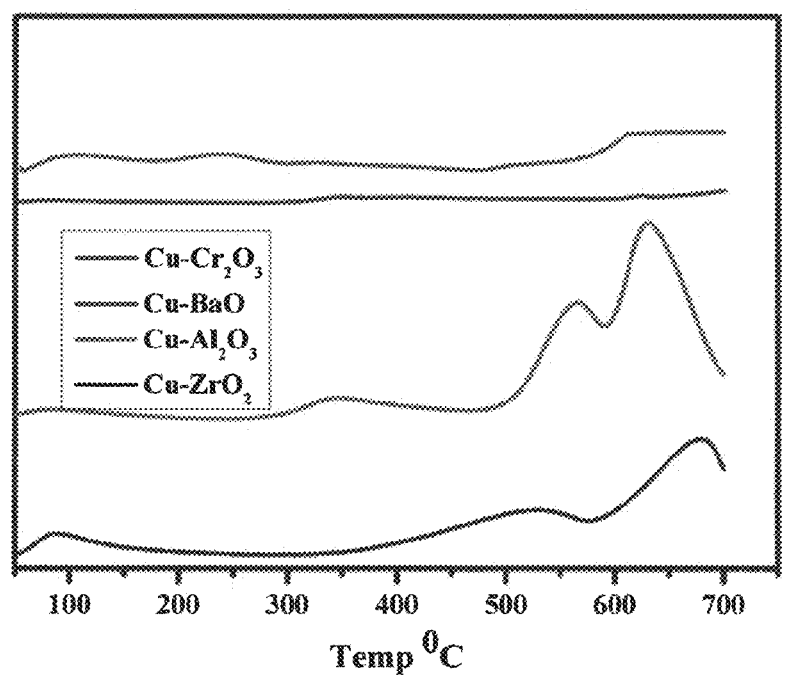
Fig. 3A
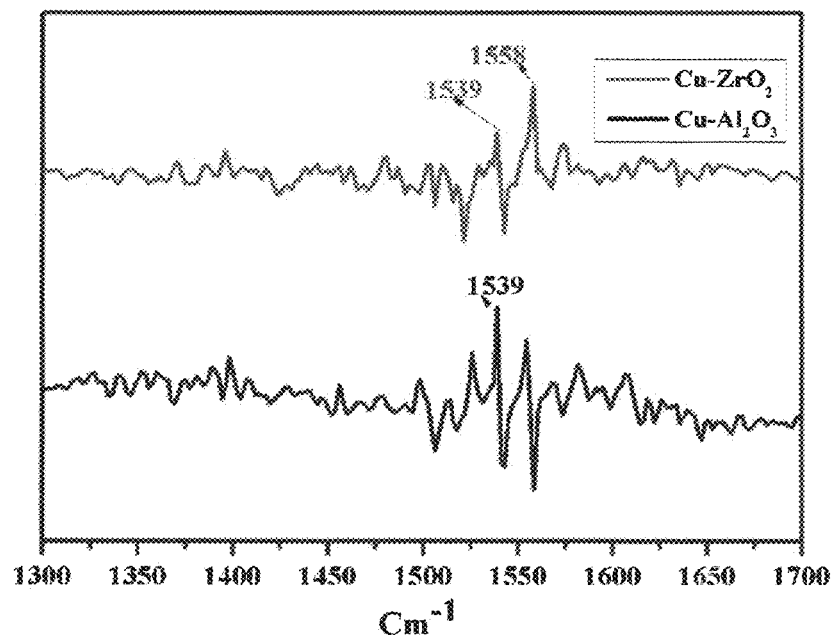
Fig: 3 B

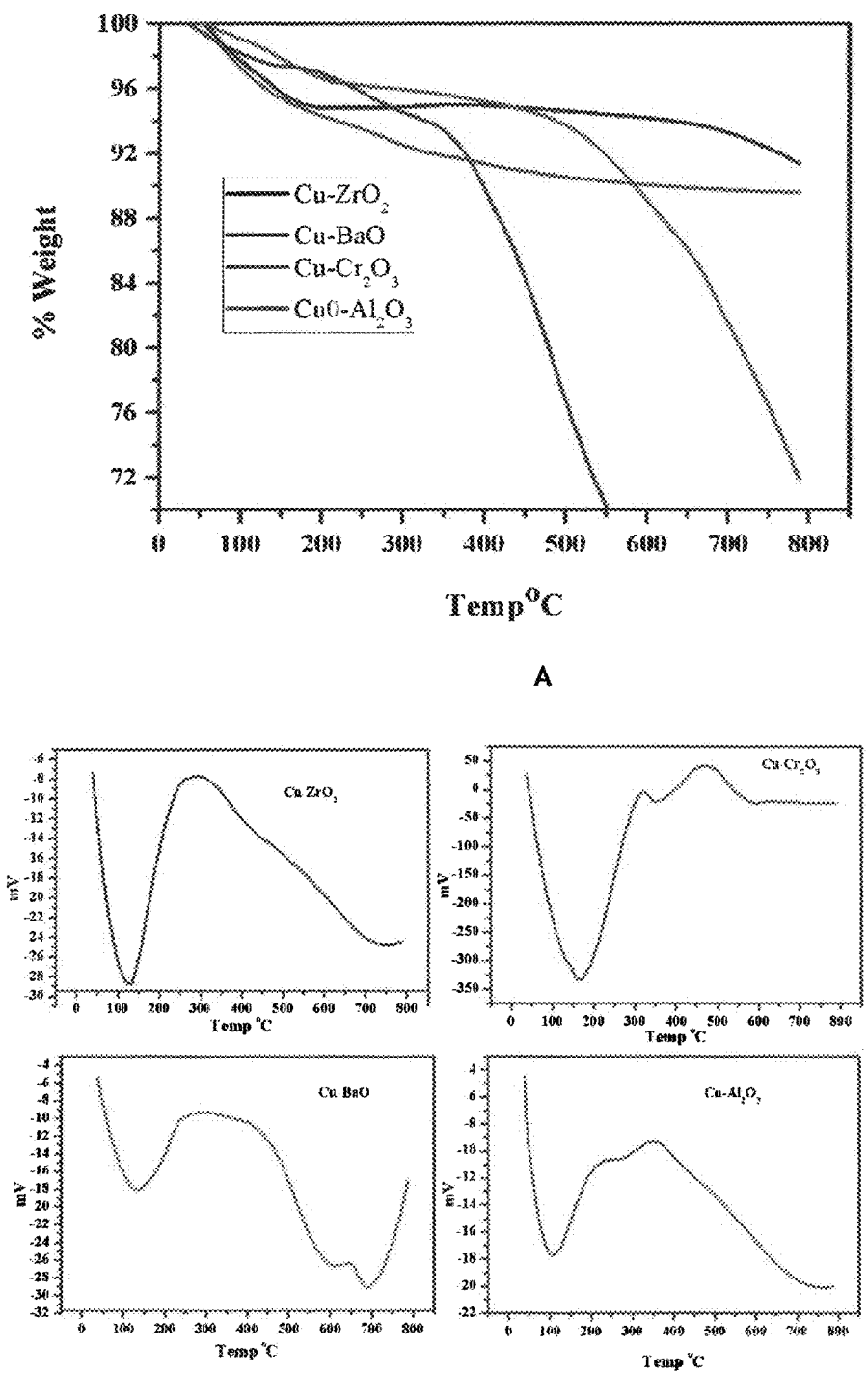
Fig: 4

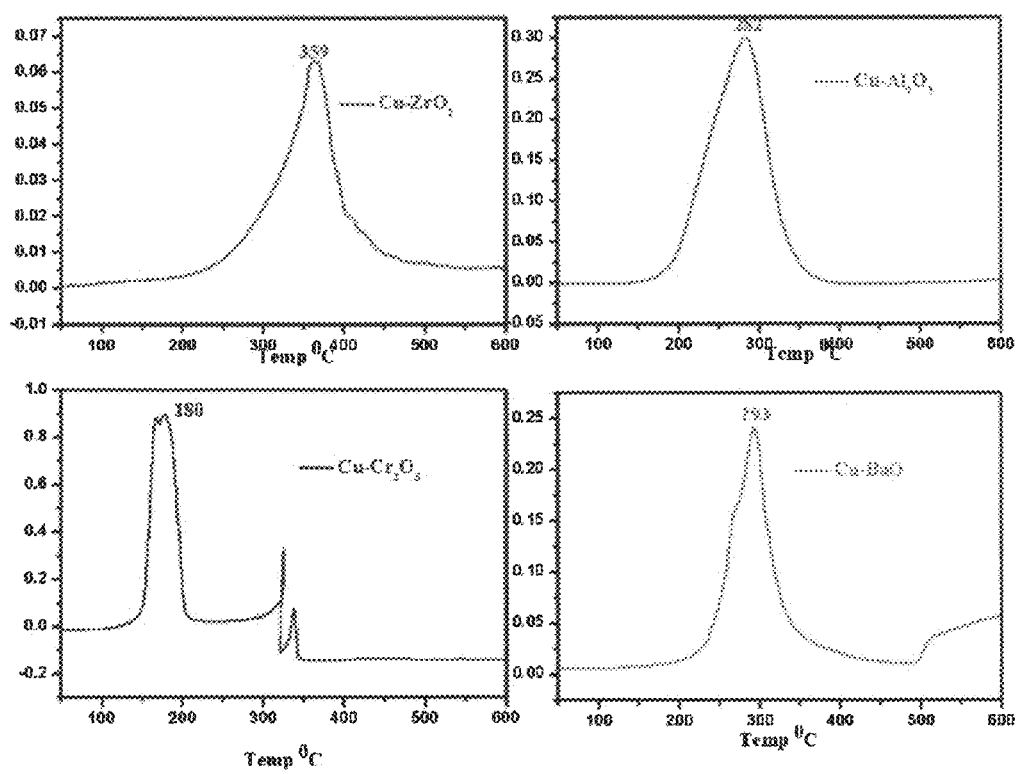
Fig: 5

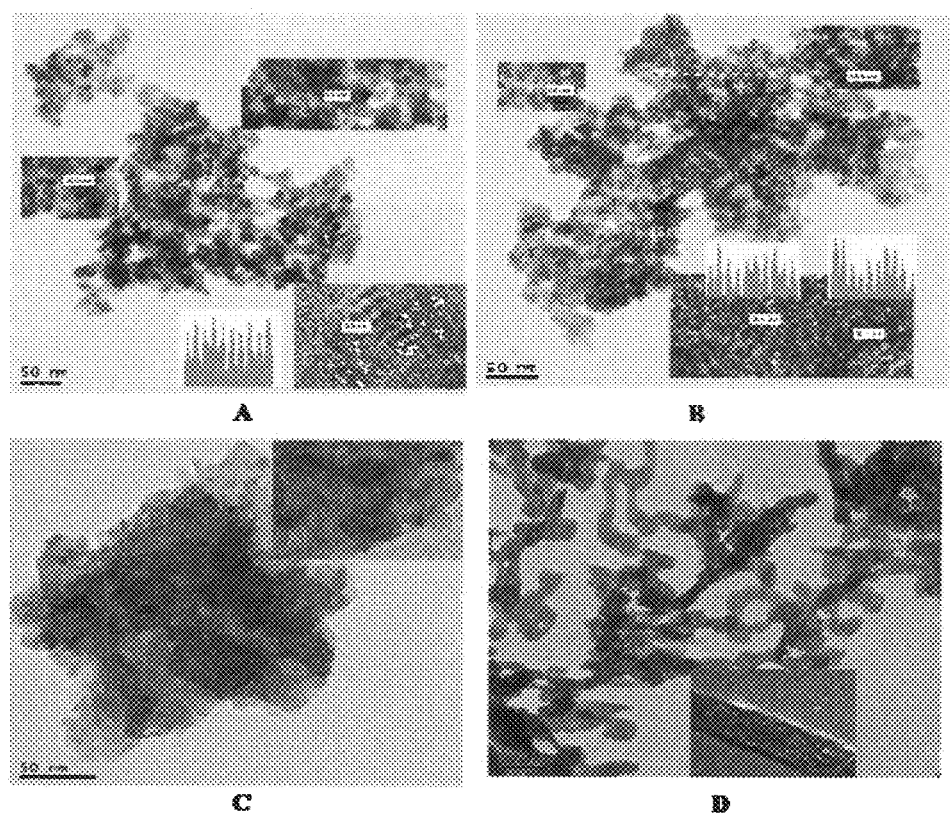
Fig: 6

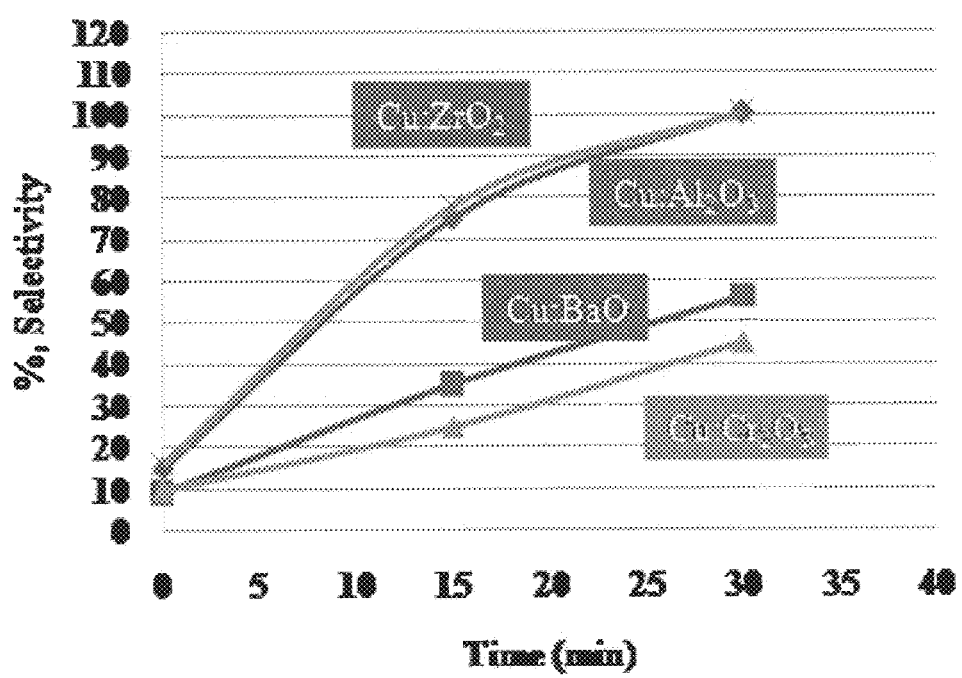
Fig: 7

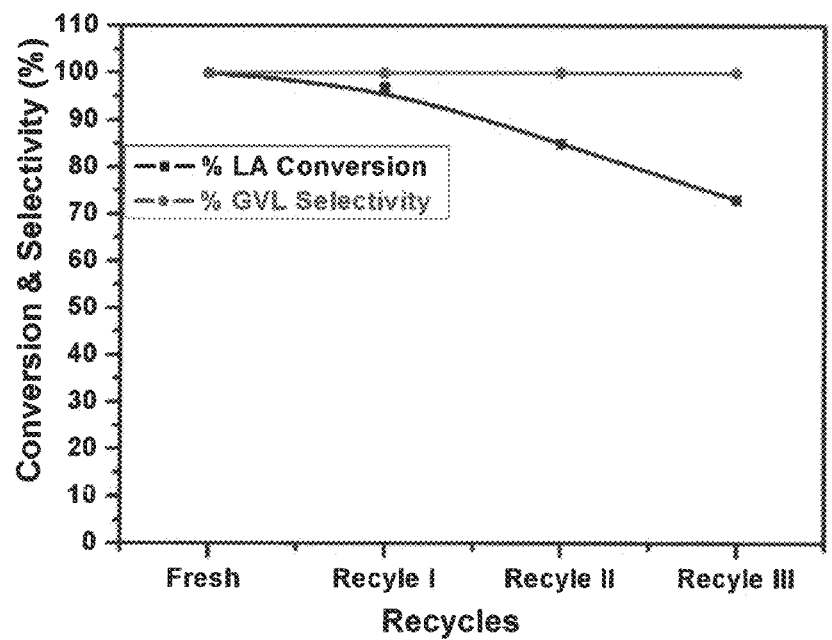
Fig: 8A
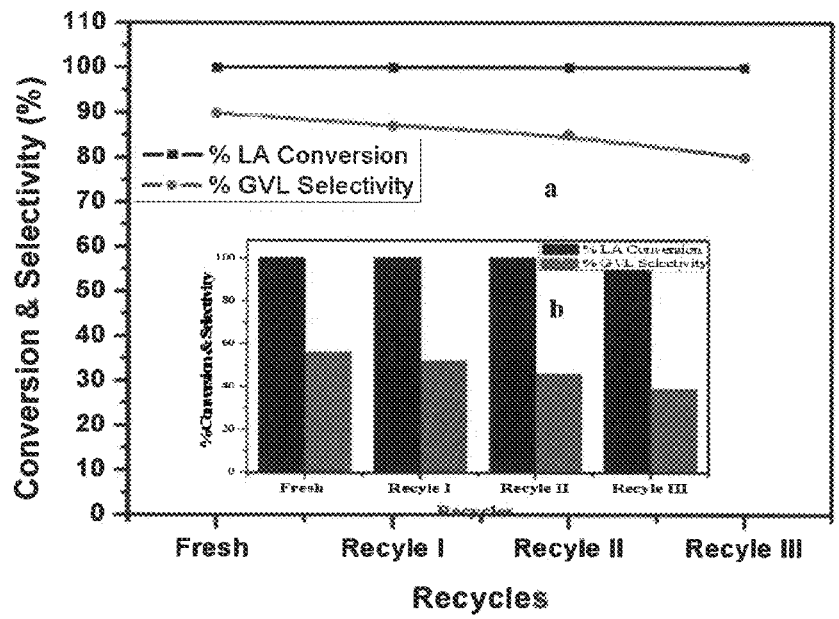
Fig 8B

Scheme 1

Scheme 2

PROCESS FOR PREPARATION OF γ-VALEROLACTONE VIA CATALYTIC HYDROGENATION OF LEVULINIC ACID

TECHNICAL FIELD OF THE INVENTION

The present invention relates to a process for preparation of γ-Valerolactone via catalytic hydrogenation of levulinic acid. In particular, the present invention relates to selective hydrogenation and subsequent cyclisation of Levulinic acid in presence of non-noble metal bi-functional catalyst to yield γ-valerolactone as bio-based platform chemical with high application potential.

BACKGROUND AND PRIOR ART OF THE INVENTION

A 'biorefinery' concept sustainably produces both fuels and chemicals from bio feedstock therefore are being matured for implementation in near future. In the first decade of 21$^{st}$ century, much research has been focused on developing new catalytic routes for the conversion of several bio based platform molecules into multiple commodity products. The presence of oxygen containing multiple functional groups, makes the bio derived molecules unique as well as they require number of processing steps as compared to the fossil derived hydrocarbons.

In 21st century oil refineries industries focused on analogous of bio-refineries to produce fuel and specialty chemicals due to shortage of fossil resources. Thus, green catalytic chemistry community is currently trying to develop new platform chemicals based on biomass as a starting material for chemical and fuel. The lignocellulosic material, which is derived from biomass is becoming one of the primary starting compound for sustainable chemistry. It can be converted by different means to a variety of compounds, such as hydrolysis to levulinic acid (LA), furfural, lactic acid etc. The new generation abundantly available lignocellulosic feedstock at lower cost can be easily converted to a variety of starting materials. For ex. hydrolysis of 5-hydroxymethyl furfural gives levulinic acid (LA) and processes have been already developed from wood, cellulose etc.

In recent years, the concept of bio-refineries similar to oil refineries is being considered so that the process economics for biofuel will be more advantageous. γ-Valerolactone (GVL) is considered a very interesting green, bio-based platform chemical with high application potential. Chemically, γ-Valerolactone is 5-Methyldihydrofuran-2(3H)-one having structural formula given below. This clear liquid is one of the more common lactones. It is a structural isomer of delta-valerolactone.

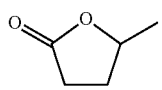

Formula I

Levulinic acid (4-Oxopentanoic acid) is a keto acid and is a white crystalline compound soluble in water, ethanol, and diethyl ether.

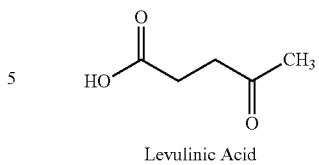

Levulinic Acid (Formula II)

Hydrogenation and subsequent cyclization of levulinic acid, either by using homogeneous or heterogeneous catalysts to γ-Valerolactone are reported in the prior arts.

Joo et al. demonstrated the use of water soluble homogeneous ruthenium catalysts with sulfonated triphenylphosphine ligands (e.g. HRuCl (Dpm)3, Dpm=diphenyl phosphinobenzene-m-sulfonic acid) for the hydrogenation of oxo- and unsaturated acids. However, catalyst activity for the hydrogenation of keto-acids like LA was low. Recently, Horv'ath and co-workers reported the use of Ru(Acac)3 in combination with TPPTS (tris(3-sulfonatophenyl)phosphine) for the hydrogenation of LA in water at 140° C. and 69 bar hydrogen. After 12 h, LA conversion was complete and GVL was obtained in essentially quantitative yield (>95%). Although most hydrogenations have been performed with molecular hydrogen in presence of heterogeneous catalysts, Haan et at. 22 showed that the hydrogenation of LA or ethyllevulinate to GVL using formic acid as the hydrogen donor with a variety of heterogeneous catalysts. But reactions were carried out in the gas phase system at 200-350° C. and pressure between 1-10 bar. The maximum yield was 81 mol % in case of ethyl levulinate as the substrate.

US2010217038 discloses a process for conversion of levulinic acid into pentanoic acid, the process comprising (a) hydrogenating levulinic acid in presence of hydrogen with a non-acidic heterogeneous hydrogenation catalyst comprising a hydrogenation metal supported on a solid catalyst carrier to obtain a first effluent comprising gamma valerolactone; (b) contacting at least part of the first effluent under hydrogenating conditions, in the presence of hydrogen, with a strongly acidic catalyst and a hydrogenation metal to obtain a second effluent comprising pentanoic acid and unconverted gamma valerolactone, and wherein part of the unconverted gamma valerolactone is recycled to step (a) and/or step (b).

US2004254384 relates to a process for producing 5-methyl-dihydro-furan-2-one from levulinic acid in presence of a supercritical fluid, and in presence of optionally-supported metal catalyst selected from the group consisting of palladium, ruthenium, rhenium, rhodium, iridium, platinum, nickel, cobalt, copper, iron, osmium, compounds thereof, and combinations thereof.

US 2003055270 relates to a process for producing 5-methylbutyrolactone from levulinic acid utilizing an optionally supported metal catalyst selected from the group consisting of carbon, SiO2, and Al2O3. The catalyst has both a hydrogenation and a ring-closing function. The metal catalyst of the invention can be selected from the group consisting of Group VII (Groups 8-10) of the Periodic Table of Elements, preferably selected from the group consisting of iridium, palladium, platinum, rhenium, rhodium and ruthenium and combinations thereof.

An article titled "Synthesis of γ-Valerolactone by Hydrogenation of Biomass-derived Levulinic Acid over Ru/C Catalyst", by Zhi-pei Yan et. al., published in Energy & Fuels, Vol. XXXX, discloses the applicability of Ru/C catalyst in the hydrogenation of LA to GVL.

Article titled "Catalytic synthesis of α-methylene-γ-valerolactone: a biomass-derived acrylic monomer" by Leo E Manzer et.al in Applied Catalysis A: General Volume 272, Issues 1-2, 28 Sep. 2004, Pages 249-256 discloses a two-step process for its synthesis from a biomass-derived starting material, levulinic acid. The first step is a high yield hydrogenation of levulinic acid to γ-valerolactone (GVL) in nearly quantitative yield using a Ru/C catalyst. The second step is a heterogeneous, gas phase catalytic condensation of formaldehyde with GVL over basic catalysts, prepared from Group 1 and 2 metal salts on silica. The said article further states that, the described process however suffers from rapid catalyst deactivation but proper choice of the catalyst provides a thermodynamically unfavorable yet desired product in good yield.

The homogeneous catalyst systems used in the hydrogenation process obviously have serious drawbacks of catalyst recovery and its recycle and multistep synthesis of ligands, thus not favorable for commercial application. Serious problem of active metal leaching/deactivation of the heterogeneous catalyst in hydrogenation of LA is also observed and reported by Lange et. al. Although carbon supports overcome the problem of leaching to some extent however do not allow for the regeneration of deactivated catalyst by coke burn-off.

Further, the reported methods which use noble metals are neither sustainable nor low-priced and has major problem of tedious operating condition, which causes serious environmental problems as well as suffers from the drawback of poor selectivity of the desired product and corrosive nature of reagents. With view to overcome the drawbacks in the use of noble metals for the hydrogenation of levulinic acid and subsequent cyclization to γ-valerolactone, it is the object of the present invention to provide a process for complete selectivity to γ-valerolactone using cost effective, efficient, non-noble catalysts.

OBJECTS OF THE INVENTION

Main object of the present invention is to provide a process for complete selectivity to γ-valerolactone Using Cost Effective, Efficient, non-noble catalysts.

Another object of the present invention is to provide a single step process under mild operating conditions thereby avoiding leaching, deactivation of the catalyst, thus making the process simple and industrially feasible.

SUMMARY OF THE INVENTION

Accordingly, present invention provides a process for preparation of compound of formula I

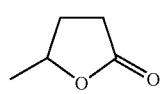

Formula I comprising of selectively hydrogenating the compound of formula II

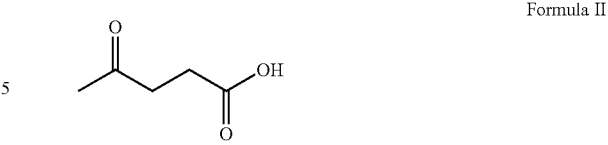

Formula II followed by subsequent cyclisation in presence of a non-noble metal bi-functional catalyst in a solvent at a temperature in the range of 453 to 653 K at pressure in the range of 435 to 580 psi, having selectivity of compound of formula I in the range of 40 to 100% and conversion of compound of formula II to compound of formula I in the range of 9 to 100%.

In an embodiment of the present invention, non-noble metal bi-functional catalyst used copper based catalyst with various promoters selected from the group consisting of Cu:Zr(1:1); Cu:Cr (1:1), Cu:Ba (1:1), Cu:Al(1:1), Cu:Cr:Al (4:4:2), Cu:Ba:Al (4:4:2) and also copper supported on carbon, silica(SiO$_2$); preferably Cu:Zr(1:1).

In another embodiment of the present invention, the catalyst used is recycled and reused.

In yet another embodiment of the present invention, the solvent used is selected from the group consisting of water, lower alcohols, acetic acid, formic acid, either alone or in combination thereof.

In yet another embodiment of the present invention, the temperature is in the range of 453 to 653 K, preferably in the range of 453 to 523 K.

In yet another embodiment of the present invention, the conversion of compound of formula II to compound of formula I in the range of 9 to 100%, preferably 80 to 100% and more preferably 100%.

In yet another embodiment of the present invention, the selectivity of compound of formula I is in the range of 40 to 100%, preferably 80 to 100% and more preferably 99 to 100%.

BRIEF DESCRIPTION OF DRAWINGS

The file of this patent contains at least one drawing or photograph executed in color. Copies of this patent with color drawing(s) or photograph(s) will be provided by the Patent and Trademark Office upon request and payment of necessary fee.

FIG. 2 Raman study of nano Cu—ZrO$_2$ catalyst (a) Activated Cu—ZrO$_2$ (b) Used Cu—ZrO$_2$ in water.

FIG. 3 NH$_3$ TPD and Py-IR profiles of copper based catalysts (A) NH$_3$ TPD profiles of copper catalysts (B) Pyridine IR of Copper with Al and Zr catalysts.

FIG. 4 TG/DTA profiles of copper based catalysts (A) TG analysis of copper catalysts (B) DTA of Copper catalysts.

FIG. 5 H$_2$ TPR profiles of copper based catalysts.

FIG. 6 HR-TEM images of nano catalyst (A) Activated Cu—ZrO$_2$ catalyst (B) used Cu—ZrO$_2$ catalyst in water (C) Activated Cu—Al$_2$O$_3$ catalyst (D) used Cu—Al$_2$O$_3$ catalyst in water.

FIG. 7 Selectivity profile for methyl levulinate formation.

FIG. 8 Recycle study of LA hydrogenation (A) conversion and selectivity pattern of LA hydrogenation in water (B) Conversion and Selectivity pattern of LA hydrogenation in methanol (a) 0.500 mg catalyst loading (b) 0.150 mg catalyst loading FIG. 9 Final reaction sample of LA hydrogenation in water and methanol (A) final reaction sample of LA in water with Cu—Al$_2$O$_3$ catalyst (B) final reaction sample of MeLA in methanol with Cu—ZrO$_2$ catalyst.
Levulinic acid, 5% (w/w); solvent, water, methanol (95 ml); Temp, 473K; catalyst, 0.5 g; (Cu—Al$_2$O$_3$, Cu—ZrO$_2$) reaction time, 5 h.

DETAILED DESCRIPTION OF THE INVENTION

Figure 1:
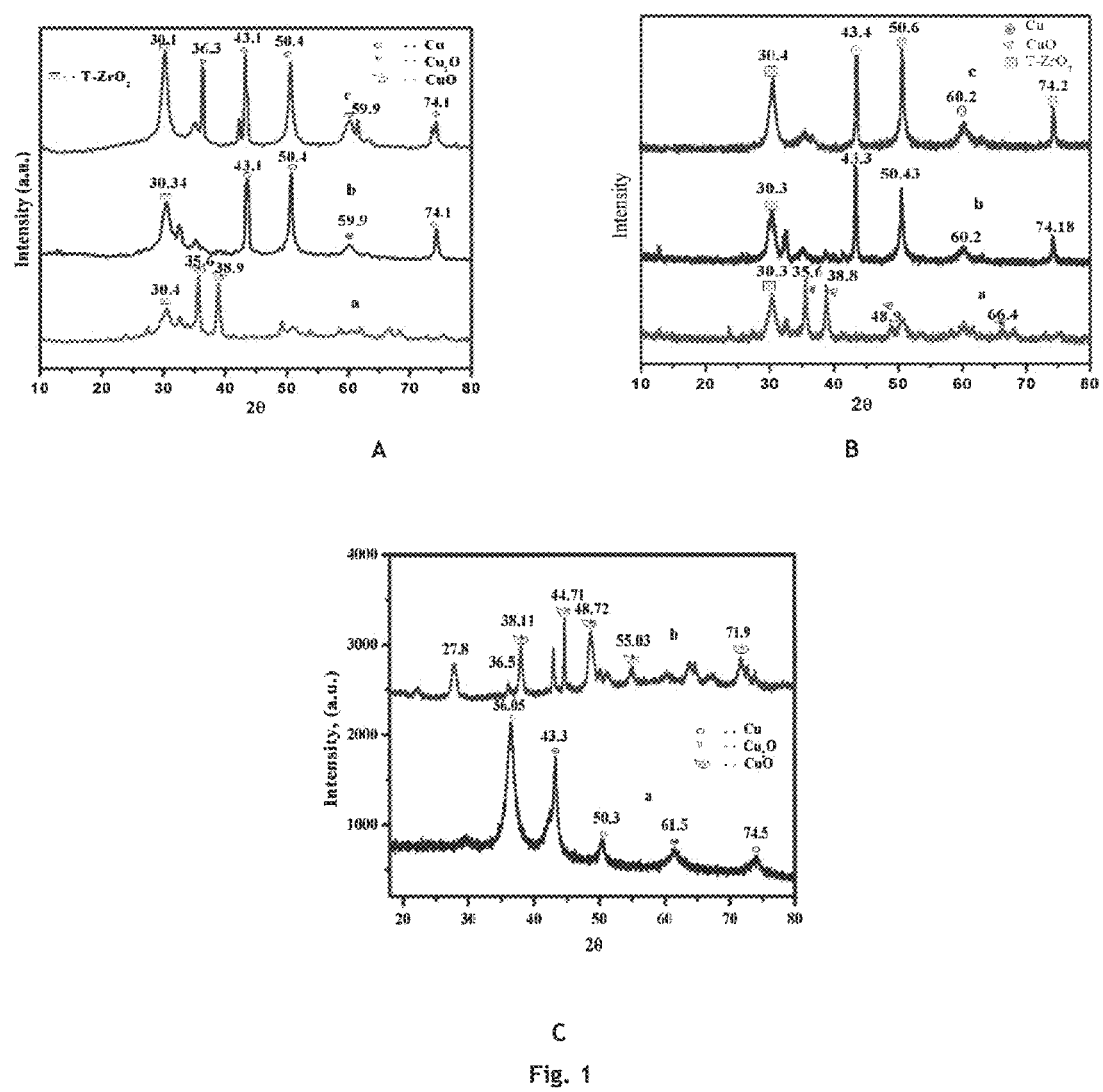
FIG. 1A XRD patterns for nano Cu—ZrO$_2$ catalyst (a) calcined Cu—ZrO$_2$ (b) Activated Cu—ZrO$_2$ (c) Used Cu—ZrO$_2$ in water.
FIG. 1B XRD patterns for nano Cu—ZrO$_2$ catalyst (a) calcined Cu—ZrO$_2$ (b) Activated Cu—ZrO$_2$ (c) Used Cu—ZrO$_2$ in methanol.
FIG. 1C XRD patterns for nano Cu—Al$_2$O$_3$ catalyst (a) Activated Cu—Al$_2$O$_3$ (b) Used Cu—Al$_2$O$_3$ in water.
Figure 9:
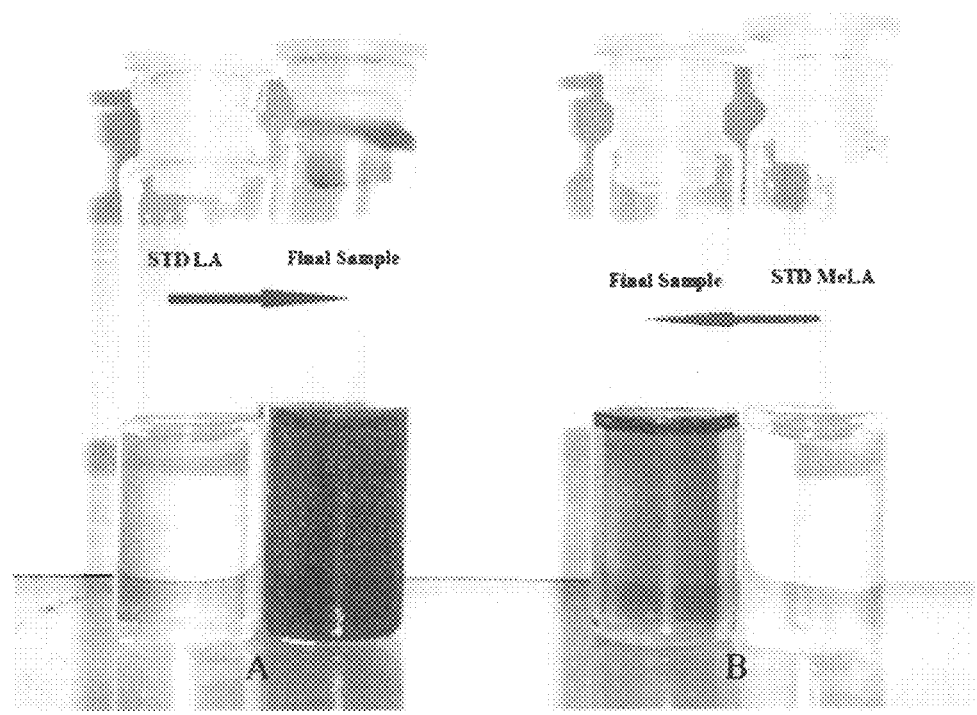
Figure 10:
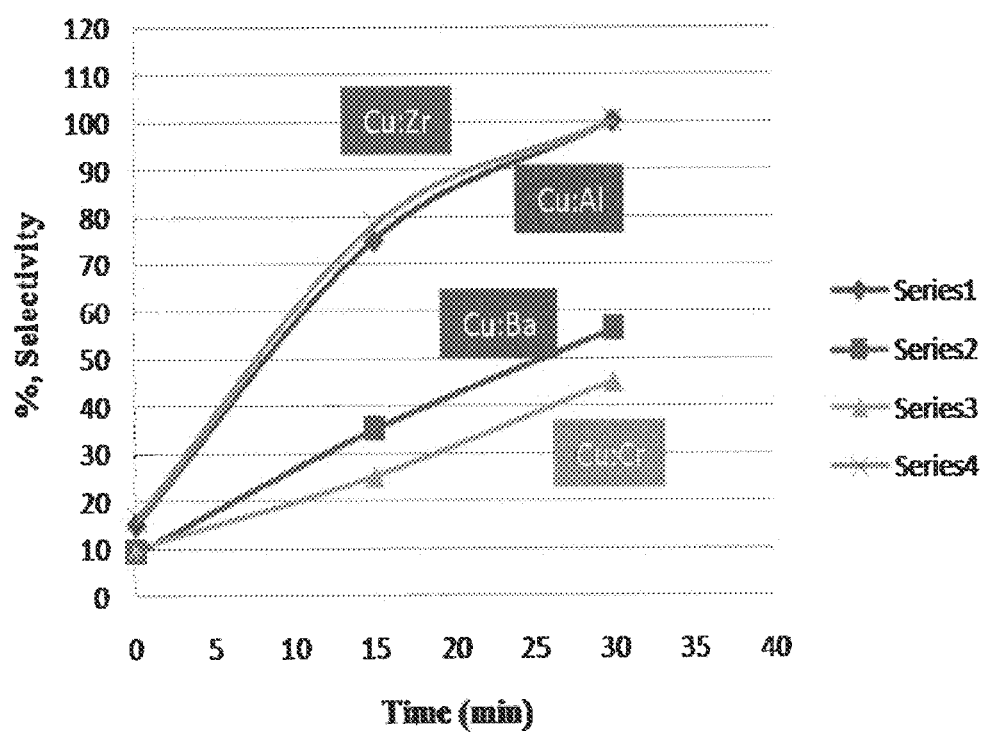
FIG. 10 depicts CT profile for methyl levulinate formation.

The present invention discloses a single step selective catalytic hydrogenation process for preparation of γ-valerolactone (GVL) via catalytic hydrogenation and subsequent cyclization of levulinic acid using a non-noble metal bi-functional catalyst under milder operating conditions. Present invention provides selective hydrogenation of levulinic acid using copper based bi-functional catalyst in presence of solvent followed by cyclization to obtain bi-functional catalyst. The catalyst of the present invention can be recycled and reused. The present invention provides γ-valerolactone with 100% selectivity catalyzed by non-noble metals, in mild conditions and in presence of a solvent.

The present invention provides single step preparation of γ-valerolactone (GVL) via selective catalytic hydrogenation and subsequent cyclization of levulinic acid using a non-noble metal bi-functional catalyst in presence of solvent selected from water, lower alcohols, acetic acid, formic acid, either alone or in combination thereof. The said solvents play a major role showing different selectivity trends in the hydrogenation of levulinic acid system.

The non-noble metal bi-functional catalyst used in the present invention is selected from copper based catalysts with various promoters such as Cu:Zr(1:1); Cu:Cr (1:1); Cu:Ba (1:1), Cu:Al(1:1), Cu:Cr:Al (4:4:2), Cu:Ba:Al (4:4:2) and also copper supported on carbon, silica(SiO$_2$); preferably Cu:Zr(1:1).

The conversion of levulinic acid to γ-valerolactone (GVL) using copper based bi-functional catalyst is carried out in presence of water. In case of aqueous system hydrogenation and dehydration of LA takes place via well-defined but unstable intermediates as described in Scheme 1. The metal-catalyzed addition of H$_2$ to the keto group of LA forms a hydroxy acid that readily undergoes intramolecular cyclization to give γ-valerolactone (GVL).

The conversion of levulinic acid to γ-valerolactone (GVL) using non-noble metal bi-functional catalyst is carried out in presence of methanol. The process includes initially transesterification of LA to give methyl levulinate which further undergoes hydrogenation of the carbonyl group of methyl levulinate to obtain 4-hydroxy methyl levulinate followed by intramolecular cyclization to form GVL. The process is described in Scheme 2.

The hydrogenation of Levulinic acid is carried out at a temperature in the range of 453-523K and with a hydrogen pressure in the range of 3-4 MPa (435-580 psi). The catalyst loading is in the range of 0.4-0.6 g and the concentration of Levulinic acid is in the range of 4.5-5.5 wt %.

The catalysts (0.5 g) used in the instant invention are pre reduced under hydrogen at 573K for 12 hours and added to levulinic acid (5 wt %) and a solvent selected from water or methanol (95 ml) in the 300 ml capacity autoclave at a stirring speed of 1000 rpm. The temperature of the mixture is maintained at 473K and the pressure of 500 psi. The stirring is continued for 5 hours. The liquid samples are withdrawn periodically and analyzed by GC.

The selectivity and the conversion rate using various copper based bi-functional catalysts is given below in Table 1 and Table 2.

The physical characteristics of γ-valerolactone obtained by the process of the present invention are characterized by NMR spectra and are given below in FIGS. 2, 3 and 4.

FIG. 2 depicts NMR spectra of γ-Valerolactone having characteristic peaks at 1H-NMR (CDCl3 200 MHz): δ1.39-1.43 (d, 3H), 1.73-1.93 (m, 1H), 2.28-2.43 (m, 1H), 2.51-2.59 (m, 2H), δ.56-4.73 (m, 1H).

FIG. 3 depicts C13 NMR spectra of γ-Valerolactone having characteristic peak at 13C NMR (CDCl3, 50 MHz): δ 20.86, 28.93, 29.50, 77.18 and 177.26.

FIG. 4 depicts DEPT C13 NMR spectra of γ-valerolactone.

With aqueous and methanol containing reaction medium and copper zirconia bifunctional as the catalyst give 100% selectivity with complete conversion while in methanol 90% highest selectivity with complete conversion respectively is observed.

The instant invention describes the way to the utilization of biomass derived compounds selected from domestic biomass resources such as pulp and paper operation, agricultural and forestry wastes, urban wood wastes, municipal solid wastes and landfill gas, animal wastes and terrestrial and aquatic crops, etc. in bio-refineries both to improve the green credentials of chemical products using low impact technologies and the utilization of cheap, readily available catalysts in chemical process.

γ-valerolactone (GVL) obtained by the process of the instant invention has great commercial value as a sustainable liquid, since it can be converted to a number of interesting derivatives such as hydrogenation of GVL provides access to methyltetrahydrofuran (MTHF), which is a potential fuel additive. The reaction of GVL and formaldehyde leads to the formation of α-methylene-γ-valerolactone (MGVL), a new acrylic monomer which may be converted to novel acrylic polymers. Further, ring-opening of GVL with methanol followed by dehydration produces methylpentenoate (MP), which is also an important monomer. Furthermore, it is considered as a potential fuel additive and is a suitable replacement for ethanol in gasoline ethanol blends.

The catalyst used in the instant invention can be reused and recycled. The catalyst reusability studies for Cu—Zr catalyst are carried out as follows. After the first hydrogenation is complete, the reaction crude is allowed to settle down and supernatant clear product mixture is removed from the reactor. A fresh charge of reactants is added to the catalyst residue retained in the reactor and the subsequent run is continued.

This procedure is followed for three subsequent runs and the results are shown in FIG. 5. The copper zirconia catalyst showed almost the same activity with slight decrease in selectivity for levulinic hydrogenation in methanol even after third recycle. A marginal decrease in selectivity from 90 to 80% could be due to sintering of active sites of metal particles. The catalyst activity dropped down to 70% in aqueous medium due to copper leaching in reaction crude.

EXAMPLES

Following examples are given by way of illustration therefore should not be construed to limit the scope of the invention.

Materials

Levulinic acid (99%), methyl levulinate were purchased from Sigma-Aldrich, Bangalore, India while methanol (>99.9%) was purchased from Rankem, India Copper nitrate, zirconium nitrate were purchased from Loba Chemie, Mumbai, India. Hydrogen (>99.99%) purity was obtained from Inox-India.

Catalyst Preparation

Copper zirconia (Cu—$ZrO_2$) catalyst was prepared by co-precipitation method. 0.05M aqueous solution of each Cu $(NO_3)_2.3H_2O$ and $Zr(NO_3)_3.3H_2O$ were taken and precipitated using 0.2 M aqueous potassium carbonate at room temperature. The precipitate was aged further for 6 h.h. at room temperature. The precipitate was separated by filtration and washed with deionized water to remove the traces of potassium. The precipitate thus obtained was dried in static air oven at 373 K for 8 h and calcined at 673 K for 4 h. Prior to the reaction, the calcined catalyst was reduced in $H_2$ pressure.

Hydrogenation Experiment and Analysis

LA hydrogenation reactions were carried out in a 300 ml capacity autoclave (Parr Instruments Co., USA) at a stirring speed of 1000 rpm. The typical hydrogenation conditions were: temperature, 473K; LA concentration, 5 wt %; catalyst loading, 0.5 g; and hydrogen pressure 500 psi. The catalysts were pre-reduced under H2 at 573K for 12 h. Liquid samples were withdrawn periodically and analyzed by GC (HP-6890) having HP-5 column with FID as detector.

tive spectra are given in the supporting information. It is observed that copper in combination with Zr and Al showed complete LA conversion in water while, copper with other metals showed very poor LA conversion in the range of 4-45%, although complete GVL selectivity was obtained in all the cases. On the other hand in methanol solvent, maximum selectivity upto 90% to GVL was achieved only in case of Cu—$ZrO_2$ and Cu—$Al_2O_3$ catalysts. Copper in combination with other metals gave LA conversion of <90% with GVL selectivity ranging from 45-86%. The lowering in GVL selectivity was observed due to unconverted 4-HMeLA and MeLA. The poor surface acidity of Cu catalysts with metals other than Zr and Al as evidenced by $NH_3$-TPD, was responsible for the slower rate of esterification. This also affected the further steps of Cu catalyzed hydrogenation and acid catalyzed cyclization to GVL leading to accumulation of 4-HMeLA and MeLA. The marginal lower selectivity to GVL in methanol over Cu—$ZrO_2$ catalyst was due to less facile cyclization of 4-hydroxylmethyl levulinate having bulkier methyl group as compared to that of 4-hydroxyl levulinic acid. The excellent catalytic performance of copper-zirconia catalyst observed is due to the following i) its strong surface acidity as well as retention of its textural properties with microporous nature of Cu—$ZrO_2$ under reaction conditions that catalyzes cyclization of the intermediate hydroxyl levulinic acid/ester due to the protonation of hydroxyl group. ii) $ZrO_2$ also plays a role in the first step of hydrogenation in which hydrogen adsorbs dissociatively on $ZrO_2$. iii) among the oxide dopents of other metals such as barium, chromium, aluminium, Zr is the most stable to "decoking" conditions during repeated catalyst regeneration cycles. iv) $ZrO_2$ shows much higher stability against its leaching in aqueous LA solution in high temperature reaction conditions, as shown by the catalyst recycles studies described below.

Figure 11:
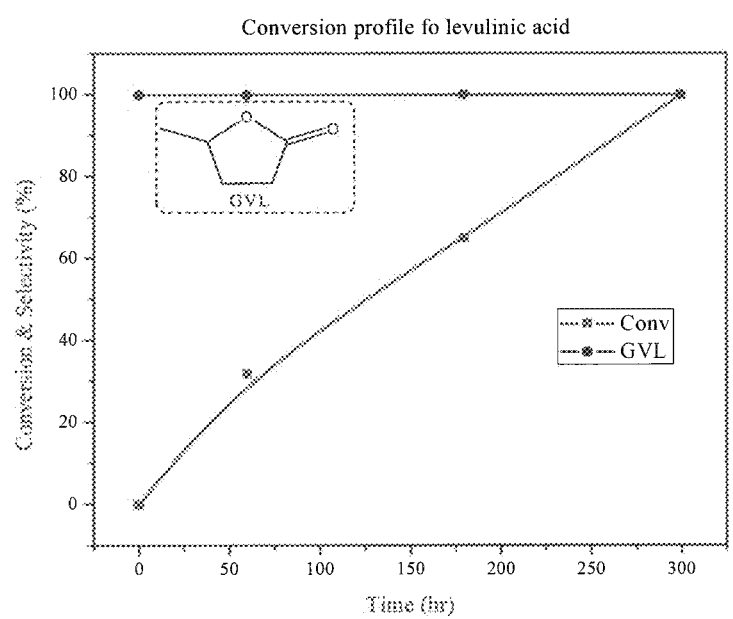
FIG. 11 depicts Conversion Vs selectivity profile of LA hydrogenation in water.

FIG. 11 shows a concentration Vs time profile for GVL formation using our copper zirconia bifunctional catalyst by keeping all parameters same. Within five hours conversion of LA to GVL was complete. No other bi product was found.

TABLE 1

Catalytic screening for hydrogenation of LA in water and methanol

| | Water | | Methanol | | | |
|---|---|---|---|---|---|---|
| | Conversion, | Selectivity, % | Conversion, | Selectivity, % | | |
| Catalysts | % | GVL | % | GVL | 4-HMeLA | MeLA |
| Cu—$ZrO_2$ (1:1) | 100 | 100 | 100 | 90 | 9 | 1 |
| Cu—$Al_2O_3$ (1:1) | 100 | 100 | 100 | 86 | 10 | 4 |
| Cu—$Cr_2O_3$ (1:1) | 9 | 100 | 72 | 45 | 20 | 35 |
| Cu—BaO (1:1) | 12 | 100 | 78 | 41 | 9 | 50 |
| Cu—$Cr_2O_3$—$Al_2O_3$ (4:4:2) | 40 | 100 | 89 | 82 | 14 | 2 |
| Cu—BaO—$Al_2O_3$ (4:4:2) | 45 | 100 | 92 | 86 | 8 | 6 |

Reaction conditions:: Levulinic acid, 5% (w/w); solvent, Water and MeOH (95 ml); Temp, 473 K; H2 pressure, 500 psi; catalyst, 0.5 g; reaction time, 5 h.

Figure 12:
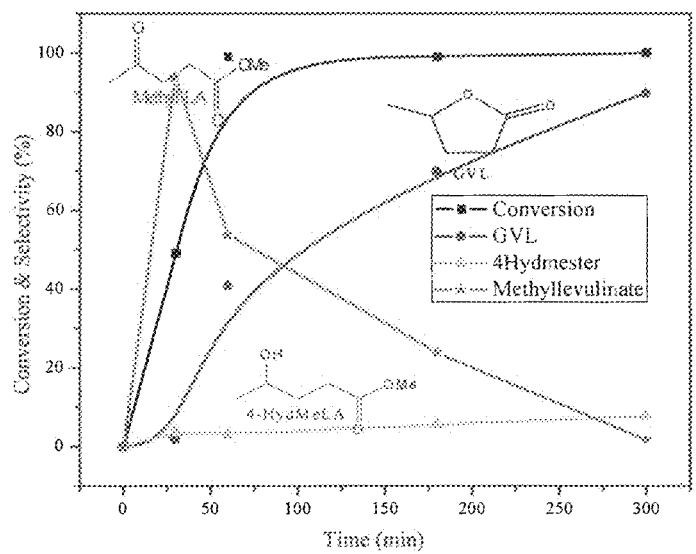
FIG. 12 depicts Conversion Vs selectivity profile of LA hydrogenation in methanol.
Figure 13:
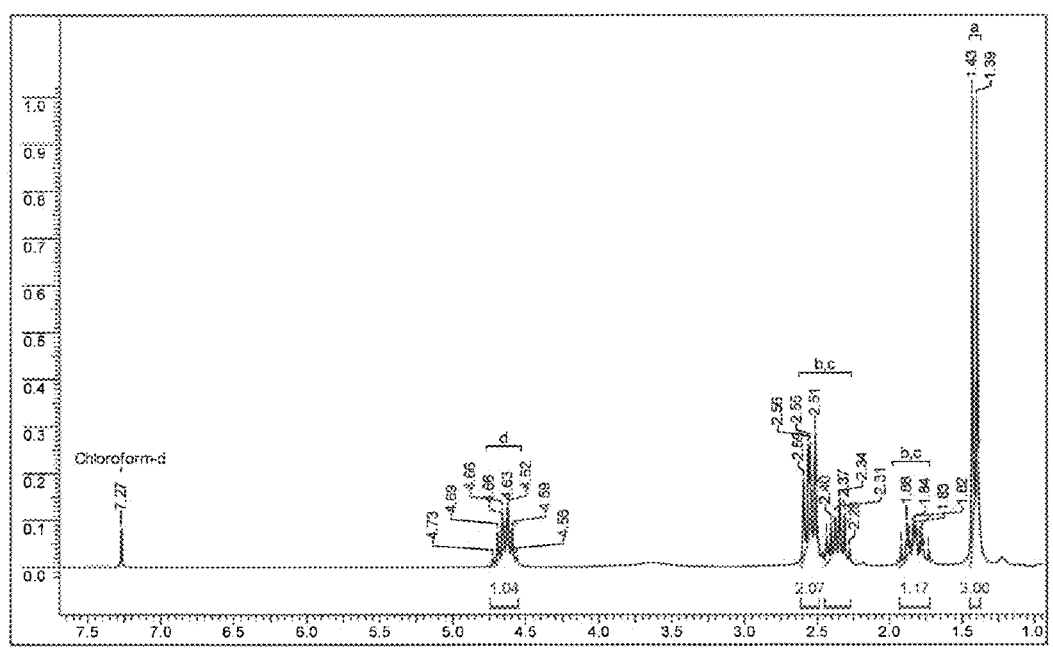
FIG. 13 depicts NMR spectra of γ-Valerolactone.
Figure 14:
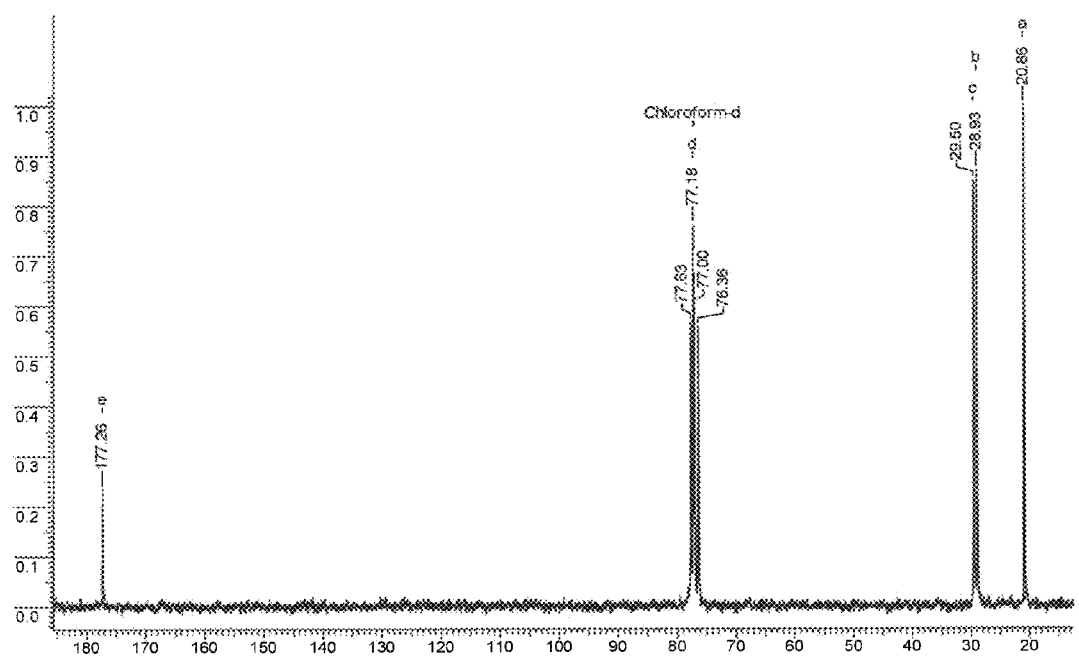
FIG. 14 depicts C$^{13}$ NMR spectra of γ-Valerolactone.
Figure 15:
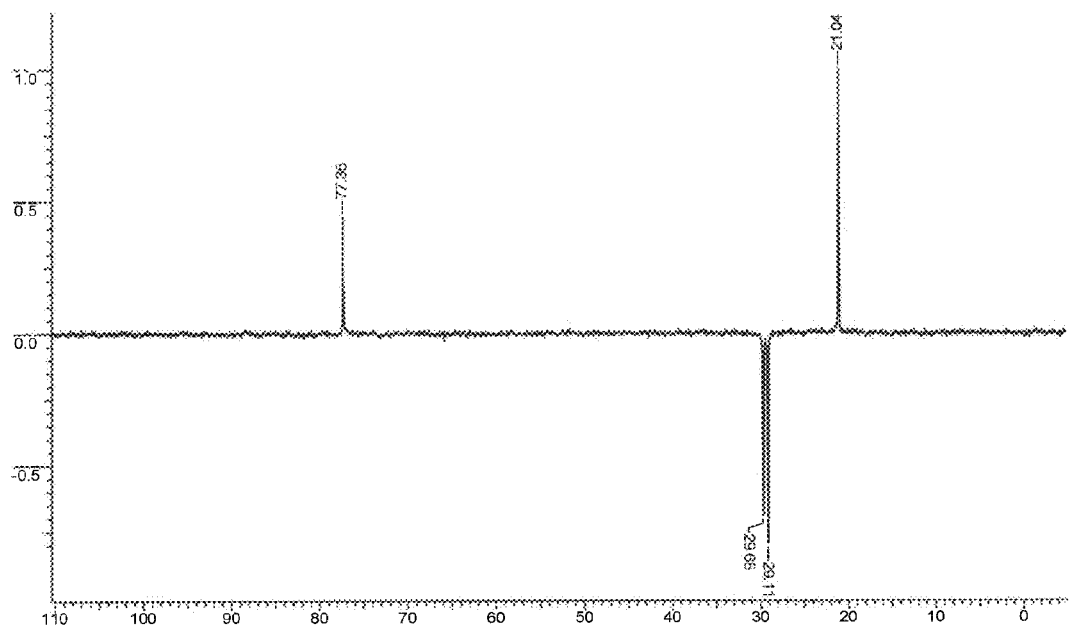
FIG. 15 depicts DEPT C$^{13}$ NMR spectra of γ-Valerolactone.
Figure 16:
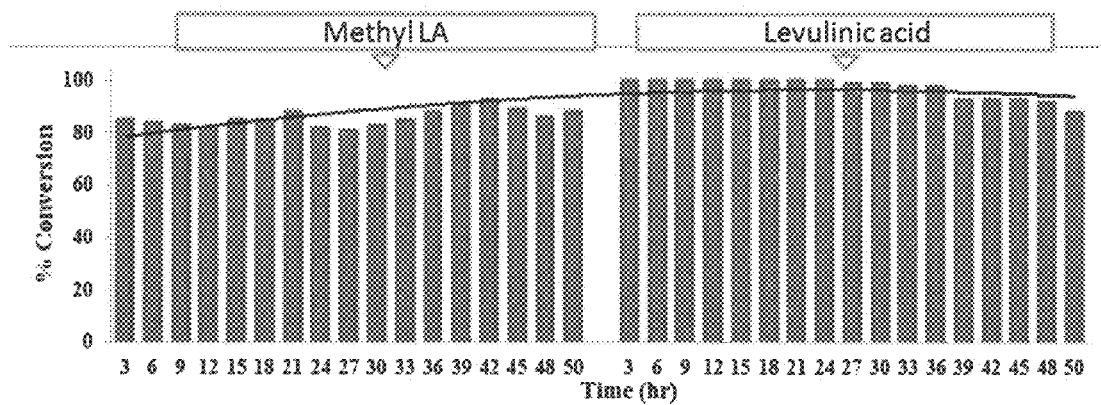
FIG. 16 depicts the (A) Reaction parameters (B) % Conversion of methyl LA and LA with time.
Figure 17:
FIG. 17 is a first reaction scheme (Scheme 1) for conversion of levulinic acid to gamma valerolactone.
Figure 18:
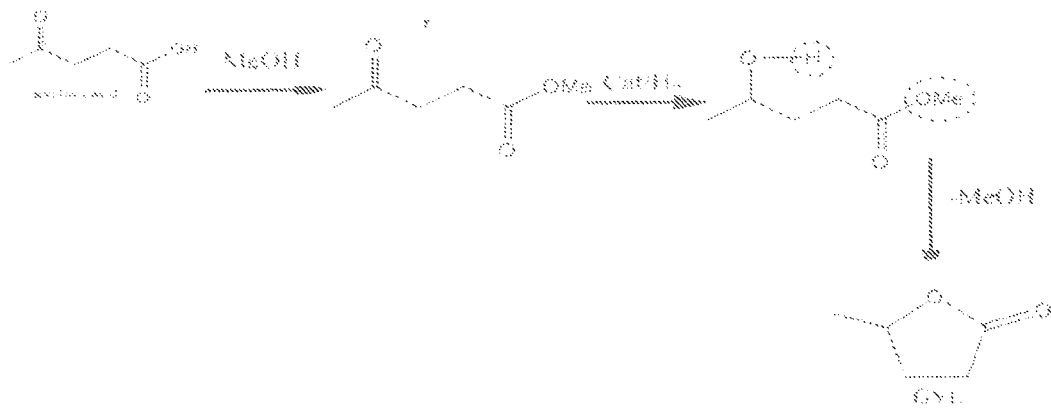
FIG. 18 is a second reaction scheme (Scheme 2) for conversion of levulinic acid to gamma valerolactone.

The preliminary results on hydrogenation of LA to GVL using various copper catalysts in both water and methanol solvents are presented in Table 1. The desired product GVL was identified by $H^1$NMR, $^{13}$C-NMR, DEPT and the respec- FIG. 12 shows distinct difference between selectivity pattern initially within 30 min methanolysis of LA to selective methyl ester further and its hydrogenation followed by cyclization to GVL. After 180 min. conversion was 99% with 70% selectivity to GVL remaining was methyl ester and 4-hydroxy methyl ester respectively finally in 300 min LA conversion was complete with highest selectivity 90% to GVL and remaining was the intermediate, 4-hydroxymethyl LA and methyl LA.

TABLE 2

Example 2: Catalytic activity and stability for synthesis of GVL

| Catalysts | Substrate | Solvent | Conversion, % | Selectivity, % | | | Metal Leaching (ppm) |
| --- | --- | --- | --- | --- | --- | --- | --- |
| | | | | GVL | Me-LA | 4-hydroxy Me-LA | |
| Cu—ZrO$_2$ | Levulinic Acid | Water | 100 | >99.9 | 0.01 | 0.01 | 34 |
| | Levulinic acid | Methanol | 100 | 90 | 2 | 8 | 2 |
| | Methyl levulinate | Methanol | 95 | 92 | SM | 8 | ND |
| | *Methyl levulinate | Methanol | 81 | 79 | SM | 21 | ND |
| Cu—Al$_2$O$_3$ | Levulinic Acid | Water | 100 | >99.9 | 0.01 | 0.01 | 174 |
| | Levulinic acid | Methanol | 100 | 86 | 4 | 10 | 31 |
| | Methyl levulinate | Methanol | 93 | 88 | SM | 12 | ND |

Reaction conditions:: LA, MeLA, (5% w/w); Temp, 473 K; H$_2$ pressure, 500 psi; catalyst, 0.5 g; reaction time, 5 h.
*Reaction conditions:: Methyl LA, (20% w/w); Temp, 473 K; H$_2$ pressure, 500 psi; catalyst, 0.5 g; reaction time, 5 h.

As the stability is very critical to the efficient use of any catalyst, Cu metal leaching was studied for Cu—ZrO$_2$ and Cu—Al$_2$O$_3$ catalysts since almost complete conversion of LA with similar selectivities to GVL were obtained for both the catalysts. The extent of Cu metal leaching was dramatically affected by the change in the reaction medium. As can be seen from Table 2, the active metal teaching was maximum (174 ppm) for Cu—Al$_2$O$_3$ catalyst while it was only 34 ppm in case of Cu—ZrO$_2$ catalyst in water medium. Even in methanol solvent, metal leaching upto 31 ppm was observed for Cu—Al$_2$O$_3$ while it was almost completely suppressed in case Cu—ZrO$_2$ catalyst.

However, no metal leaching was observed when methyl levulinate was used as a substrate inspite of the substrate loading was increased from 5 to 20% w/w. Copper metal leaching was also evident from the blue color of the reaction crude in case of Cu—Al$_2$O$_3$ catalyzed reaction due to the formation of a metal carboxylate complex with levulinic acid. This was also confirmed by FT-IR in which the frequency of carbonyl group of levulinic acid shifted from 1702 cm$^{-1}$ to 1565 cm$^{-1}$ as against no change was observed for methyl levulinate as a substrate. Thus metal leaching could be avoided at least in case of Cu—ZrO$_2$ in presence of methanol where carboxyl group undergoes trans-esterification thus, rendering unavailability of a free carboxylic group to form a soluble copper complex. The proposed reaction mechanism as shown in Scheme 1, is believed to proceed differently in methanol than that in water. In presence of methanol, first step of trans-esterification of carboxyl group forms methyl levulinate and its subsequent hydrogenation to GVL involves elimination of methanol that can be recycled. As against this in water, first step is direct hydrogenation of keto group to give 4-hydroxy levulinic acid followed by its dehydration to give cyclic GVL.

Catalyst Characterization

X-ray diffraction patterns were recorded on a PAnalytical PXRD Model X-Pert PRO-1712, using Ni filtered Cu Kα radiation (λ=0.154 nm) as a source (current intensity, 30 mA; voltage, 40 kV) and X-celerator. detector. The samples were scanned in the 2θ range of 20-80°.

The crystallite size was determined by Scherrer equation.

$$D = k\lambda/B \cos\theta$$

The Raman spectra of sample were recorded on a Horiba JY Lab RAM HR800 micro-Raman spectrometer with 17 mW 632.8 nm laser excitation.

NH$_3$-TPD experiments were carried out on a Chemisoft TPx (Micromeritics-2720) instrument. In order to evaluate acidity of the catalysts, ammonia TPD measurements were carried out by: (i) pre-treating the samples from room temperature to 300° C. under helium flow rate of 25 mL/min. (ii) adsorption of ammonia at 50° C. (iii) desorption of ammonia with a heating rate of 10° C. min$^{-1}$ starting from the adsorption temperature to 973 K. Py-IR spectra were recorded on shimadzu FTIR 8000 attached with SSU (Second sampling unit) using 20 mg catalyst sample. Sample was filled in a sample cup, 20 mL of pyridine were injected in N$_2$ flow. FTIR spectra were recorded on a Perkin-Elmer instrument. The pellets for analysis were prepared by mixing 2 mg of the catalyst with 150 mg of KBr. FTIR spectra were recorded between 400 to 4000 cm$^{-1}$ with accumulation of 20 scans and 4 cm$^{-1}$ resolution.

Thermo gravimetric analysis (TG/DTA) were performed on Perkin-Elmer TGA-7 analyzer at a 10° C./min scan rate in nitrogen atmosphere starting from room temperature to 800° C. TPR experiments of prepared Copper catalysts were also performed on a Chemisoft TPx (Micromertics-2720) In the TPR experiment, a U-tube (Quartz tube) was filled with solid catalyst. This sample holder was positioned in a furnace equipped with a temperature control. A thermocouple was placed in the solid for temperature measurement. Equal quantity of fresh vacuum dried catalyst was taken in the U-tube. Initially, flow of inert gas (Argon) was passed through U-tube to remove the air present in the lines, and heated in Ar atmosphere with a flow rate of 25 mL/min to 200° C. for 30 min to remove the moisture and surface impurities present on the sample and then it was cooled to room temperature. Ar was replaced by a mixture of 5% H$_2$ in Ar gas for the TPR experiment with a heating rate of 10° C. min$^{-1}$ starting from the room temperature to 700° C. and a thermal conductivity detector (TCD) measured the hydrogen uptake.

The particle size and morphology were studied using transmission electron microscope (HR-TEM), model JEOL 1200 EX. A small amount of the solid sample was sonicated in 2-propanol for 1 min. A drop of prepared suspension was deposited on a Cu grid coated with carbon layer and grid was dried at room temperature before analysis. The sample analysis of metal leaching experiments was carried out by using instrument (ICP-OES), the supernatant liquid was evaporated and resulting solid was treated with aqua regia ($HNO_3$:HCl=1:3), 60° C. on a sand bath for 2 h and than made up to 25 mL by distilled water.

Catalyst Recycling Study

In order to establish catalyst recycling, studies for hydrogenation of LA were carried out with copper zirconia as the catalyst by keeping all parameters same. When the reaction was completed it was settled down, decanted the product liquid, and added fresh charge for next run. This procedure was repeated for three subsequent runs and the result shown in the copper zirconia catalyst showed significant activity after third recycle. The LA conversion was slight dropdown from 100 to 83%. This was due to the sintering of active sites of metal particle and change in phase of zirconia from tetragonal to semi crystalline.

TABLE 3

Literature summary on hydrogenation of LA

| | | | Reaction conditions | | | | | |
|---|---|---|---|---|---|---|---|---|
| Sr. No. | Sub. | Catalyst | Temp (K) | $H_2$Press (psi) | Time (h) | % conversion | % Product distribution | Reference |
| 1 | Levulinic acid | 5% Pt/Silica | 523 | 650 | 3 | 100 | 4 (GVL), 92 (pentatonic acid), 4 (Me—THF) | US0217038 (2010) |
| 2 | Levulinic acid | 5% Ru/$Al_2O_3$ | 423 | 1500 | 2 | 99 | 99.5(GVL) | US0254384 (2004) |
| 3 | Levulinic acid | 5% Ru/Calicat C | 488 | 800 | 2 | 100 | 97 (GVL) | US0055270 (2003) |
| 4 | Levulinic acid | 5% Ru/C | 423 | 800 | 2 | 100 | 97 (GVL) | Appl. Catal. A 272, 2004, 249-256 |
| 5 | Levulinic acid | 5% Ru/C | 403 | 200 | 4 | 92 | 99 (GVL) | Energy & Fuels |
| 6 | Levulinic acid | Ru(acac)$_3$ + TPPTS | 473 | 1200 | 6 | 100 | 37 (GVL), 63(1,4PDO) | Top. Catal. 48 (2008) 49-54 |
| 7 | Levulinic acid | Pd/$Al_2O_3$ | 493 | — | 12 | — | 29 (GVL) Yield | Green Chem. 12, 2010, 656-660 |
| 8 | Fructose | Ru/C + TFA, RuCl3/PPh3 | 453 | — | 16 | — | 52 (GVL) Yield | Green Chem. 11, 2009, 1247-1255 |
| 9 | Levulinic acid | Raney Ni | 493 | 700 | 3 | — | 94 (GVL) | J. Am. Chem. Soc. 69, 1947, 1961-1963. |
| 10 | Levulinic acid | 5% Ru/$SiO_2$ | 473 | 1450 | — | 99 | 99 (GVL) Yield | Chem. Commun. 2007, 4632-4634 |

Optimization Study

To optimize stability and activity for continuous hydrogenation of levulinic acid and its ester over Cu—ZrO2 catalyst in fixed bed reactor using methanol as a solvent. The hydrogenation of methyl levulinate and levulinic acid was carried using zirconia supported copper catalysts for 100 h. It shows complete conversion (<99%) with 80-95% selectivity to g-valerolactone (GVL), this confirmed that alcoholic medium hydrogenation of LA and its ester showed stability and highest activity and selectivity over non noble catalytic systems.

In conclusion, the preset invention elucidates two pathways for hydrogenation of levulinic acid by using different solvents in presence of non-noble bifunctional copper zirconia catalysis. The bi-functional copper catalyst proved to be very active and selective in the process due to interaction of zirconia to the copper catalyst and outstanding water-tolerant properties of the catalyst promoter. The novel methodology describes the way to the utilization of biomass derived compounds in bio refineries both to improve the green credentials of chemical products using low impact technologies and the utilization of cheap, readily available catalyst in chemical processes.

ADVANTAGES OF THE INVENTION

1. Selectivity to γ-valerolactone using cost effective, efficient, non-noble catalysts.
2. Single step process under mild operating conditions
3. Avoids leaching, deactivation of the catalyst,
4. Process is simple and industrially feasible.
5. Catalyst is recyclable.

We claim:
1. A process for preparation of compound of formula I

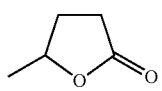

Formula I comprising of selectively hydrogenating the compound of formula II

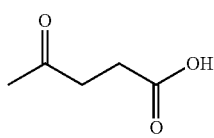

Formula II followed by subsequent cyclisation in presence of a non-noble metal bi-functional catalyst wherein said catalyst comprises copper and a metal oxide wherein the atomic ratio of copper to the metal of the metal oxide is selected from the group consisting of Cu:Zr in a ratio of about 1:1; Cu:Cr, in a ratio of about 1:1; Cu:Ba in a ratio of about 1:1, Cu: Al in a ratio of about 1;1, Cu:Cr:Al in a ratio of about 4:4:2, Cu:Ba:Al in a ratio of about 4:4:2 in a solvent at a temperature in the range of 453 to 653 K at pressure in the range of 435 to 580 psi, having selectivity of compound of formula I in the range of 40 to 100% and conversion of compound of formula II to compound of formula I in the range of 9 to 100%.

2. The process according to claim 1, wherein the catalyst used is recycled and reused.

3. The process according to claim 1, wherein the solvent used is selected from the group consisting of water, lower alcohols, acetic acid, formic acid, either alone or in combination thereof.

4. The process according to claim 1, wherein the temperature is in the range of 453 to 653 K.

5. The process according to claim 1, wherein the conversion of compound of formula II to compound of formula I is in the range of 9 to 100%.

6. The process according to claim 1, wherein the selectivity of compound of formula I is in the range of 40 to 100%.

7. The process according to claim 1 wherein the copper-based non-noble metal bifunctional catalyst is a copper-zirconium oxide catalyst with an atomic ratio of copper:zirconium 1:1.

8. The process according to claim 4 wherein the temperature is in the range of about 453 to about 523 K.

9. The process according to claim 5 wherein the conversion of compound of formula II to formula I is in the range about 80 to about 100%.

10. The process according to claim 9 wherein the conversion is about 100%.

11. The process according to claim 1 wherein the selectivity of compound of formula I is in the range about 80 to 100%.

12. The process according to claim 11 wherein the selectivity of compound of formula I is in the range about 99 to 100%.

13. The process according to claim 1 wherein the copper-based non-noble metal bifunctional catalyst is a copper-aluminum oxide catalyst with an atomic ratio of copper:aluminum 1:1.

* * * * *